United States Patent [19]

Kondo et al.

[11] 4,245,108

[45] Jan. 13, 1981

[54] PROCESS FOR PREPARING 2-THIO-2-SUBSTITUTED-ALKANOIC ACID DERIVATIVES

[75] Inventors: Kiyosi Kondo, Yamato; Daiei Tunemoto, Sagamihara; Akira Negishi, Yamato; Minoru Suda, Sagamihara, all of Japan

[73] Assignee: Sagami Chemical Research Center, Tokyo, Japan

[21] Appl. No.: 934,553

[22] Filed: Aug. 17, 1978

[30] Foreign Application Priority Data

Aug. 18, 1977 [JP] Japan .................................. 52-98271
Sep. 7, 1977 [JP] Japan .................................. 52-106826

[51] Int. Cl.$^3$ .................. C07C 149/40; C07D 333/24
[52] U.S. Cl. ........................................ 549/79; 560/15; 562/426
[58] Field of Search ................... 260/329 R; 562/426; 549/78, 79, 80; 560/15

[56] References Cited

U.S. PATENT DOCUMENTS 2,445,356 7/1948 Kharasch et al. ................... 562/426

OTHER PUBLICATIONS

Reeve, Wilkins et al., J. Am. Chem. Soc., 82 pp. 4062-4066, (1960).
Ibid vol. 83 pp. 2755-2759 (1961).
Patai, Saul, "The Chemistry of Carboxylic Acids and Esters", (1969), Interscience Publ., pp. 388-389, and 730-733.
Furet, Christian et al., "A New Aspect of the Reactivity of Tetrahalomethyltrialkyltins: Aldehyde Addition", J. Organomet. Chem., (1975), 102(4), 423-430, (See Chem. Abstracts vol. 84, (1976), at #89,514a).
Juby, P. F. et al., J. of Medicinal Chemistry, 15(2), pp. 1297-1306 (1972).
Luknitskii, F. I., Chemical Reviews 75(3) at p. 269, (1975).
Kirk-Othmer, "Encyclopedia of Chemical Technology", Interscience Publ., vol. 12, p. 851 (1967), vol. 15, p. 214 (1969).
Patai, Saul, "The Chemistry of the Ether Linkage", Interscience Publ., pp. 559-560, (1967).
Clemence, Francois et al., "Recherche de Composes Anti-Inflammatoires et Analgesiques dans la Serie du Thiophene", Eur. J. Med. Chem. Chimica Therapeuri, Jul.-Aug. 1974-1979, No. 4, pp. 390-396.
Combes, Georges, "Note sur une Nouvelle Preparation de la 2-Thenaldehyde . . . ", Bull. Soc. Chim., France (1952).

Primary Examiner—Natalie Trousof
Assistant Examiner—L. Hendriksen
Attorney, Agent, or Firm—Sughrue, Rothwell, Mion, Zinn and Macpeak

[57] ABSTRACT

A process for preparing a 2-thio-2-substituted-alkanoic acid derivative represented by the formula (I)

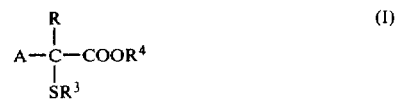

wherein A, R, $R^3$ and $R^4$ are as defined hereinafter, which comprises condensing an aldehyde compound of the formula (V)

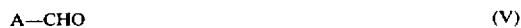

wherein A is as defined hereinafter, with a haloform of the formula $CHX_3$ wherein X is as defined hereinafter and a mercaptan compound of the formula (IV)

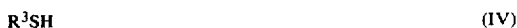

wherein $R^3$ is as defined hereinafter, in the presence of a base to produce a 2-(arylthio or alkylthio)-2-substituted-acetic acid of the formula (III)

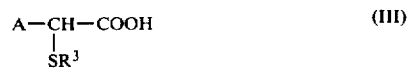

wherein A and $R^3$ are as defined hereinafter, and reacting the resulting 2-(arylthio or alkylthio)-2-substituted-acetic acid of the formula (III) with an alkylating agent represented by the formula (II)

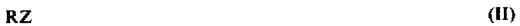

wherein R and Z are as defined hereinafter, in the presence of at least 2 mols of a base per mol of the 2-(arylthio or alkylthio)-2-substituted-acetic acid, to form the compound of the formula (I) wherein $R^4$ represents a hydrogen atom and, optionally, converting the resulting compound to the compound of the formula (I) wherein $R^4$ represents an alkyl group by esterification.

7 Claims, No Drawings

PROCESS FOR PREPARING 2-THIO-2-SUBSTITUTED-ALKANOIC ACID DERIVATIVES

BACKGROUND OF THE INVENTION

1. Field of the Invention

This invention relates to a process for preparing 2-thio-2-substituted-alkanoic acid derivatives represented by the formula (I)

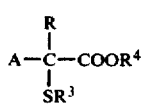

wherein A represents (1) a substituted-phenyl group of the formula

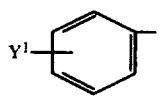

in which $Y^1$ represents an unsubstituted or substituted-phenoxy group wherein the substituent is a halogen atom, a trifluoromethyl group or an alkoxy group having 1 to 4 carbon atoms, or (2) a substituted-thienyl group of the formula

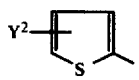

in which $Y^2$ represents an alkyl group having 1 to 4 carbon atoms; R represents an alkyl group having 1 to 4 carbon atoms; $R^3$ represents a phenyl group, an alkylphenyl group wherein the alkyl group has 1 to 4 carbon atoms, or an alkyl group having 1 to 4 carbon atoms; and $R^4$ represents a hydrogen atom or an alkyl group having 1 to 4 carbon atoms, which are useful as intermediates for the synthesis of various pharmaceutical agents.

2. Describtion of the Prior Art

Hitherto, salicyclic acid derivatives, pyrazolone derivatives, indomethacin, etc. have been used widely as anti-inflammatory agents. These agents generally exhibit a potent anti-inflammatory activity, but they also tend to cause serious side-effects such as gastro-intestinal disorders, adverse affects on hematosis, etc. upon administration.

Recently, various alkanoic acid derivatives such as 2-(3-phenoxyphenyl)alkanoic acid compounds have been interesting because of their low possibility of causing side-effects, while the anti-inflammatory activity thereof is not so potent, thereby making it possible to administer these agents over a prolonged period of time to patients.

The compounds of the formula (I) wherein A represents a 3-phenoxyphenyl group can be easily converted into the above 2-(3-phenoxyphenyl)alkanoic acid compounds. Also, the compounds of the formula (I) wherein A represents a substituted-thienyl group can be easily converted, upon reduction, into an α-(2-thienyl)alkanoic acid which can then be converted into thiobrophenic acid having an anti-inflammatory activity, as disclosed in Japanese Patent Publication (Examined) No. 24915/74. Further some esters of the above α-(2-thienyl)alkanoic acid are known to have a high insecticidal activity, as disclosed in Japanese Patent Publication (Unexamined) No. 126826/74.

Typical conventional processes for preparing 2-(phenoxyphenyl)alkanoic acid derivatives represented by the formula (I) wherein A represents a substituted-phenyl group includes (1) a process comprising heat-refluxing a 3-phenoxyacetophenone derivative with sulfur in the presence of a secondary amine to process a 3-phenoxyphenylacetic acid derivative, condensing the resulting compound with a carbonic acid ester to form an arylmalonic acid ester, introducing an alkyl group into the ester, followed by hydrolysis and decarbonization to obtain the desired compound, as disclosed in Japanese Patent Publication (Examined) No. 45586/76; (2) a process comprising converting a 3-phenoxy-halobenzyl derivative as a starting material into a corresponding cyano compound, then into an alkoxycarbonyl compound, and alkylating, hydrolyzing and decarbonizing the resulting compound in the same manner as described for the process (1) above to obtain the desired compound, as disclosed in Japanese Patent Publication (Examined) No. 45586/76; (3) a process comprising reducing a 3-phenoxyacetophenone derivative followed by halogenation to obtain a 1-(3-phenoxyphenyl)haloethyl, and converting the resulting compound into a corresponding nitrile derivative and then hydrolyzing the nitrile derivative, as disclosed in Japanese Patent Publication (Examined) No. 70744/76; and (4) a process comprising converting the 1-(3-phenoxyphenyl)-haloethyl used in the above process (3) into a Grignard compound and reacting the Grignard compound with carbon dioxide to produce the desired compound, as disclosed in Japanese Patent Publication (Unexamined) No. 65729/76.

However, the above conventional processes are not considered advantageous in the production on an industrial scale for the reasons that these processes require a number of reaction steps to produce the desired compounds; the starting material, an acetophenone derivative, used in the processes (1), (3) and (4) is not easily available as an industrial raw material; a highly toxic hydrocyanic acid derivative must be used as a reagent in the processes (2) and (3); and an absolutely anhydrous condition must be used in preparing the Grignard compound in the process (4).

Also, typical conventional processes for preparing α-(2-thienyl)alkanoic acid derivatives of the formula (I) wherein A represents a substituted-thienyl group include (1) a process comprising alkylating an α-(2-thienyl)cyanoacetic acid ester, followed by decarbonization to produce an α-(2-thienyl)alkanenitrile and then hydrolyzing the nitrile group, as disclosed in M. Bercot-Vatteroni, R. C. Moreau and P. Reynaud Bull. Soc. Chim., France, 1820 (1961); and (2) a process comprising condensing a thiophene with ethyl chloroglyoxarate, and reacting the resulting condensate with a Grignard compound followed by reduction, as disclosed in F. Clemence, O. Le Martret, R. Fournex, G. Plassard and M. Dagnaux, Eur. J. Med. Chem., (1974-9), 390.

However, these processes require a number of complicated reaction steps and therefore cannot be advantageously applied to the production on an industrial scale.

DETAILED DESCRIPTION OF THE INVENTION

As a result of extensive studies on the process for preparing the compounds of the formula (I) which can easily be converted into the corresponding 2-substituted-alkanoic acid compounds, the present inventors established a process for preparing the compounds of the formula (I), starting with easily available compounds through 3 to 4 reaction steps which can be relatively easily performed.

The term "an alkyl group having 1 to 4 carbon atoms" as used herein includes straight and branched chain alkyl groups having 1 to 4 carbon atoms.

That is, the present invention provides a process for preparing 2-thio-2-substituted-alkanoic acid derivatives represented by the formula (I)

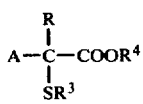
(I)

wherein A represents (1) a substituted-phenyl group of the formula

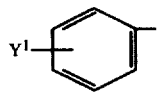

in which $Y^1$ represents an unsubstituted- or substituted-phenoxy group wherein the substituent is a halogen atom, a trifluoromethyl group or an alkoxy group having 1 to 4 carbon atoms, or (2) a substituted-thienyl group of the formula

in which $Y^2$ represents an alkyl group having 1 to 4 carbon atoms; R represents an alkyl group having 1 to 4 carbon atoms; $R^3$ represents a phenyl group, an alkylphenyl group wherein the alkyl group has 1 to 4 carbon atoms, or an alkyl group having 1 to 4 carbon atoms; and $R^4$ represents a hydrogen atom or an alkyl group having 1 to 4 carbon atoms, which comprises condensing an aldehyde compound of the formula (V)

(V)

wherein A is as defined above, with a haloform of the formula $CHX_3$ wherein X represents a halogen atom and a mercaptan compound of the formula (IV)

(IV)

wherein $R^3$ is as defined above, in the presence of a base to produce a 2-(arylthio or alkylthio)-2-substituted-acetic acid of the formula (III)

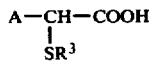
(III)

wherein A and $R^3$ are as defined above, and reacting the resulting 2-(arylthio or alkylthio)-2-substituted-acetic acid with an alkylating agent represented by the formula (II)

$$RZ \quad (II)$$

wherein R is as defined above, and Z represents a halogen atom, an alkyl- or arylsulfonyloxy group or a sulfuric acid ester residual group, in the presence of at least 2 mols of a base per mol of the 2-(arylthio or alkylthio)-2-substituted acetic acid, to form the compound of the formula (I) wherein $R^4$ represents a hydrogen atom, and optionally converting the resulting compound to the compound of the formula (I) wherein $R^4$ represents an alkyl group by esterification.

The process according to the present invention can be illustrated by the following reaction scheme:

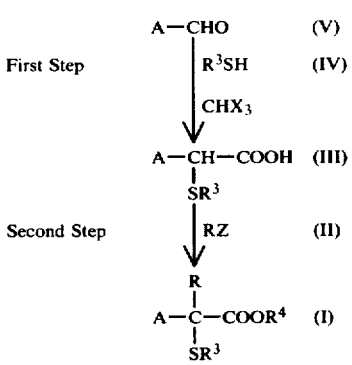

wherein A, R, $R^3$ and $R^4$ are as defined above, and X represents a halogen atom and Z represents a halogen atom, and alkyl or arylsulfonyloxy group or a sulfuric acid ester residual group.

First Step

The first step of the process of this invention comprises condensing an aldehyde derivative of the formula (V) with a haloform of the formula $CHX_3$ wherein X is as defined above and a mercaptan compound of the formula (IV) in the presence of a base.

Examples of the base which can be used in the above condensation reaction are alkali metal hydroxides such as sodium hydroxide, potassium hydroxide and the like, alkali metal alkoxides such as sodium methoxide, potassium methoxide, sodium ethoxide, potassium ethoxide and the like, with sodium or potassium hydroxide being preferred from the economical standpoint. These bases are generally used in an amount of from about 4 to about 10 mols, preferably 5 to 6 mols, per mol of the aldehyde derivative of the formula (V).

Examples of the haloform of the formula $CHX_3$ are chloroform, bromoform, monobromodichloromethane, monochlorodibromomethnae and the like. Particularly preferred haloforms are chloroform and bromoform. These haloforms can be used in an amount of from about 1 to about 5 mols, preferably 1.5 to 2 mols, per mol of the aldehyde derivative of the formula (V).

Examples of the mercaptan compounds of the formula (IV) are thiophenol, alkylphenyl mercaptans such as tolyl mercaptan, alkyl mercaptans such as methyl mercaptan, ethyl mercaptan, butyl mercaptan and the like. These mercaptans can be used in an amount of from about 1 to about 3 mols, preferably 1.5 to 2 mols, per mol of the aldehyde derivative of the formula (V).

In carrying out the first step of the process of this invention, a solvent can be preferably used. Typical examples of the solvents which can be used are polar solvents such as water, alcohols such as methanol, ethanol and the like, dimethyl sulfoxide, dimethylformamide and the like. Preferred solvents are protonic solvents such as water, methanol, ethanol, etc. because of their high solubility of the base used in the reaction. The reaction can be generally conducted at a temperature of about 0° to about 100° C., preferably from room temperature (about 15° to about 30° C.) to a refluxing temperature of the solvent used. The reaction time varies depending upon the reaction temperature used, but is usually for about 1 to about 30 hours.

In the above condensation, the desired intermediate, 2-(arylthio or alkylthio)-2-substituted-acetic acids of the formula (III) can be obtained in high yield. The resulting intermediate of the formula (III) can be used in the subsequent step after it is isolated from the reaction mixture and purified by conventional procedures, for example, concentration of the reaction mixture, extraction with a solvent and then silica gel column chromatography, etc., or the reaction mixture per se obtained by the condensation reaction can be used in the subsequent step.

Second Step

The second step comprises reacting the 2-(arylthio or alkylthio)-2-substituted-acetic acid of the formula (III) obtained in the above First Step with an alkylating agent of the formula (II) in the presence of at least 2 mols, preferably 2 to 3 mols, of a base per mol of the compound of the formula (III).

Examples of alkylating agents used in the above reaction are methyl iodide, methyl bromide, ethyl bromide, dimethylsufuric acid, diethylsulfuric acid, methyl p-toluenesulfonate, ethyl p-toluenesulfonate, propyl bromide, isopropyl bromide, butyl bromide and the like. The alkylating agents are well known in the art as widely used in organic chemistry and can easily be available as industrial raw materials.

The alkylation reaction can preferably carried out at a temperature of about −40° to room temperature for a period of about 1 to about 5 hours using an approximately equimolar to a slightly molar excess of alkylating agent, e.g., about 1.5 mol, per mol of the compound of the formula (III).

As described above, the reaction should be carried out in the presence of at least 2 mols of a base per mol of the compound of the formula (III). In this reaction, 1 mol of the base is consumed in the formation of a carboxylic acid salt and the remaining 1 mol of the base is used for withdrawing the hydrogen atom at the α-position of the carboxylic acid of the formula (III). In the dianion thus formed, an alkyl group is selectively introduced into the α-position of the dianion upon reaction with an alkylating agent because of a high reactivity of the α-position thereby forming the desired compound of the formula (I)

Examples of bases which can be used in the second step are preferably strongly basic compounds such as sodium amide, potassium amide, butyl lithium, sodium hydride and the like.

In carrying out the reaction, a solvent is preferably used and examples of solvents are liquid ammonia, ethers such as diethyl ether, tetrahydrofuran and the like, non-protonic polar solvents such as dimethylformamide, dimethylsulfoxide and the like.

When sodium amide or potassium amide is used as a base, liquid ammonia is preferably used as a solvent, and when butyl lithium or sodium hydride is used as a base, an ether or a non-protonic polar solvent is preferably used.

In the above reaction, the desired compounds of the formula (I) wherein $R^4$ represents a hydrogen atom can be obtained in high yield. These compounds can easily be converted into the corresponding esters wherein $R^4$ represents an alkyl group by a conventional esterification procedure which is well known in the art.

The aldehyde compounds of the formula (V) used as starting materials of the process of this invention are well known as described in reference 21 (Rieche et al, Org. Syn., 47, 1 (1967)) of J. Med. Chem. 15, 1297 (1972); Japanese Patent Publication (Unexamined) No. 95623/77; and Org. Synth. Coll. Vol. III, 811. Also, these aldehyde compounds can be easily prepared by either the Vilsmeier formylation reaction or the oxidation of the corresponding benzyl alcohol, as well known in the art.

As described previously, the compounds of the formula (I) prepared in accordance with the process of this invention can be converted into the corresponding α-substituted-alkanoic acid of the formula (VI)

wherein A, R and $R^4$ are as defined above, by reducing the compounds of the formula (I) as described in detail in Reference Examples hereinafter described. The reduction of the compounds of the formula (I) can be achieved by various methods which are well known in the art using, for example, zinc powder in a lower aliphatic acid, tin in a mineral acid, Raney nickel, sodium metal in a protonic solvent, etc. A particularly preferred reduction method is using zinc powder in a lower aliphatic acid such as acetic acid. In this manner, the compounds of the formula (IV), for example, α-(2-thienyl)alkanoic acid, 2-(3-phenoxyphenyl)propionic acid, etc. can be obtained in almost quantitative yield.

Alternatively, the compounds of the formula (III) can be subjected to the above reduction procedure, before alkylation in the second step, to produce the corresponding acetic acid compounds of the formula (VI) wherein R represents a hydrogen atom.

As is apparent to one skilled in the art, one of the advantages of the process of this invention is that, in the reduction of the compounds of the formula (I) to produce the compounds of the formula (VI), an arylthio or alkylthio group $-SR^3$ is split out to form a mercaptan compound as a by-product. Such mercaptan compound can be recovered for re-use in the first step of the process of this invention, whereby the process of this invention can be conducted economically.

The present invention is further illustrated by the following Examples in greater detail, but they are given for illustrative purposes only and are not to be construed as limiting the present invention. Unless otherwise indicated, all parts, percents, ratios and the like are by weight.

EXAMPLE 1

A mixture of 1.98 g (10 mmols) of 3-phenoxybenzaldehyde, 1.65 g (15 mmols) of thiophenol, 1.79 g (15 mmols) of chloroform and 2 ml of ethanol was stirred at room temperature (about 15° to 30° C.), and 10 ml of an ethanolic solution of 2.8 g (50 mmols) of potassium hydroxide was then added dropwise to the mixture while maintaining the temperature below 45° C. The reaction mixture was further stirred for an additional one hour at 45° C. and then allowed to stand overnight at room temperature while stirring. The reaction mixture was then poured into a mixture of 6 N sulfuric acid and ice clump to render the mixture acidic and then saturated with sodium chloride. The saturated solution was then extracted with diethyl ether and the extract was concentrated. The resulting concentrate was then charged into a silica gel column, and the column was eluted first with benzene-hexane (1:1 by volume) and then with hexane-ethyl acetate (4:1 by volume). The combined eluate was concentrated to obtain 2.58 g (77% yield) of 2-phenylthio-2-(3-phenoxyphenyl)acetic acid. NMR (CCl$_4$) $\delta$ of Product: 4.68 (1H, s), 6.7–7.4 (14H, m), 11.6 (1H, bs).

EXAMPLE 2

In the same manner as described in Example 1, but using a reaction temperature not exceeding 30° C., 1.68 g (50% yield) of 2-phenylthio-2-(3-phenoxyphenyl)acetic acid was obtained.

EXAMPLE 3

1.10 g of 3-phenoxybenzaldehyde, 1.65 g of thiophenol and 1.8 g of chloroform were dissolved in 5 ml of ethanol, and to the resulting solution was added dropwise a solution of 2.0 g of potassium hydroxide in 10 ml of ethanol over a period of 90 minutes. The reaction mixture was then stirred overnight at room temperature and then worked up in the same manner as described in Example 1 to obtain 1.10 g (65% yield) of 2-phenylthio-2-(3-phenoxyphenyl)acetic acid.

EXAMPLE 4

1.10 g (5 mmols) of 3-phenoxybenzaldehyde, 0.83 g (7.5 mmols) of thiophenol, 1.3 g (5.1 mmols) of bromoform, 1.7 g (26 mmols) of potassium hydroxide (having a purity higher than 85%) and 0.424 g (10 mmols) of lithium chloride were added to a mixture of 5 ml of dioxane and 5 g of ice crump, and the resulting mixture was stirred vigorously for 5 hours at 0° C. and then 19 hours at room temperature. The reaction mixture was then diluted with water, rendered acidic with hydrochloric acid and extracted with methylene chloride. The extract was washed with water, dried over anhydrous magnesium sulfate and concentrated to remove the solvent to obtain a crude product of 2-phenylthio-2-(3-phenoxyphenyl)acetic acid in a quantative yield. The resulting crude product was purified by column chromatography eluting with hexane-diethyl ether (10:1 by volume) to obtain 1.54 g (92% yield) of the above product in a substantially pure form.

EXAMPLE 5

In the same manner as described in Example 1, but using 1.35 g of isobutyl mercaptan in place of the thiophenol, 1.40 g (44% yield) of 2-isobutylthio-2-(3-phenoxyphenyl)acetic acid was obtained.

NMR (CCl$_4$) $\delta$ of Product: 0.93 (6H, d, J=7 Hz), 1.62 (1H, m), 2.40 (2H, d, J=7 Hz), 4.53 (1H, s), 6.8–7.4 (9H, m).

EXAMPLE 6

15 ml of liquid ammonia was charged into a 50 ml flask and 0.2 g (8.7 mmols) of sodium metal was dissolved therein in the presence of a catalytic amount of ferric nitrate thereby forming a liquid ammonia suspension of sodium amide. Thereafter, 1.22 g (3.63 mmols) of 2-phenylthio-2-(3-phenoxyphenyl)acetic acid prepared as described in Example 1 dissolved in 10 ml of diethyl ether was added dropwise to the above suspension of sodium amide. The reaction mixture was then stirred for 30 minutes at a temperature of −40° C. and a solution of 0.75 g (5.3 mmols) of methyl iodide in 5 ml of diethyl ether was added to the reaction mixture which was then stirred for further 30 minutes at −40° C. The reaction mixture was then allowed to warm slowly by removing the cooling bath used and finally heated while refluxing for 15 minutes to complete the reaction. 30 ml of water was added to the reaction mixture to dissolve any solid substances and the mixture was rendered acidic with 1 N hydrochloric acid followed by being extracted with diethyl ether. The etherial extract was dried over anhydrous sodium sulfate and concentrated to obtain 1.23 g of a crude 2-phenylthio-2-(3-phenoxyphenyl)propionic acid. The resulting crude product was then purified by silica gel column chromatography eluting with diethyl ether-hexane (1:5 by volume) to obtain 1.10 g (87% yield) of the above product in a substantially pure form.

NMR (CCl$_4$) $\delta$ of Product: 1.76 (3H, s), 6.7–7.3 (14H, m).

EXAMPLE 7

In the same manner as described in Example 6, but using 0.67 g of diemthylsulfuric acid in place of the methyl iodide, 2-phenylthio-2-(3-phenoxyphenyl)propionic acid was obtained in 83% yield.

EXAMPLE 8

A portion of the product of Example 6, 2-phenylthio-2-(3-phenoxyphenyl)propionic acid, was esterified using diazomethane to obtain a corresponding methyl ester in a quantative yield.

NMR (CCl$_4$) $\delta$ of Product: 1.73 (3H, s), 3.68 (3H, s), 6.6–7.4 (14H, m).

EXAMPLE 9

6.80 g (103 mmols) of potassium hydroxide (85% purity) was dissolved in 20 ml of methanol, and the resulting solution was added dropwise to a solution of 2.24 g (20.0 mmols) of thiophenealdehyde, 3.5 g (30.0 mmols) of chloroform and 3.30 g (30 mmols) of thiophenol in 10 ml of methanol over a period of 30 minutes at room temperature. The resulting reaction mixture was stirred at room temperature for 1 hour, and heated while refluxing for 1 hour. Most of the solvent was removed by distillation under reduced pressure, and the residue was dissolved in water. The solution was rendered acidic with hydrochloric acid, and extracted with methylene chloride. The organic layer was dried over anhydrous magnesium sulfate and purified by silica gel column chromatography eluting with diethyl ether-hexane (1:5 by volume) to obtain 2.03 g (41% yield) of α-phenylthiothiophene-2-acetic acid.

EXAMPLE 10

0.69 g (30 milli atom) of sodium metal was added to 30 ml of liquid ammonia, and a catalytic amount of ferric nitrate was added to the solution followed by stirring at −40° C. until the blue color of the mixture disappeared. A solution of 2.52 g (10.1 mmols) of α-phenylthio-thiophene-2-acetic acid in 10 ml of diethyl ether was added dropwise to the above mixture, followed by stirring at −40° C. for 30 minutes. A solution of 2.80 g (19.7 mmols) of methyl iodide in 5 ml of diethyl ether was added dropwise thereto, and the reaction mixture was stirred for further 30 minutes at −40° C. The cooling bath was removed and the mixture was then stirred overnight to remove ammonia. The resulting solid was then dissolved in water, and the solution was rendered acidic with hydrochloric acid and extracted with methylene chloride. The extract was dried over anhydrous magnesium sulfate and the solvent was removed by distillation to obtain 2.61 g (98% yield) of a crude product. The crude product thus obtained was then purified by silica gel column chromatography using a relatively short column eluting with diethyl ether-hexane (1:5 by volume) to obtain 2.55 g (98% yield) of α-phenylthio-α-(2-thiophene)propionic acid in a substantially pure form.

NMR (CCl₄) δ of Proudct: 1.87 (3H, s), 6.7-7.1 (8H, m), 11.85 (1H, s).

EXAMPLE 11

7.50 (113.8 mmols) of potassium hydroxide was dissolved in 20 ml of methanol, and the solution was added dropwise to a solution of 2.24 g (20.0 mmols) of thiophenealdehyde, 4.78 g (40.0 mmols) of chloroform and 2.71 g (30.0 mmols) of t-butyl mercaptan in 10 ml of methanol at room temperature over a period of 1 hour. After stirring for 16 hours at room temperature, the mixture was diluted with water and washed with methylene chloride. The mixture was then rendered acidic with hydrochloric acid and extracted with methylene chloride. The extract was dried over anhydrous mangesium sulfate, concentrated and purified by silica gel column chromatography eluting with diethyl ether-hexane (1:5 by volume) to obtain 1.09 g (24% yield) of α-t-butylthio-α-(2-thiophene)acetic acid.

NMR (CCl₄) δ of Product: 1.37 (9H, s), 4.67 (1H, s), 6.73-7.23 (3H, m), 11.37 (1H, bs).

REFERENCE EXAMPLE 1

330 mg of methyl 2-phenylthio-2-(3-phenoxyphenyl)-propionate obtained in Example 8 was dissolved in 2 ml of acetic acid and the solution was heated while refluxing for 1 hour in the presence of 300 mg of zinc powder. After allowing the reaction mixture to cool, it was diluted with ethyl acetate and the remaining zinc powder was removed by filtration. The filtrate was concentrated to obtain methyl 2-(3-phenoxyphenyl)propionate in a quantative yield.

$n_D^{26}$ 1.5576.

NMR (CCl₄) δ of Product: 1.43 (3H, d, J=7.5 Hz), 3.57 (1H, q, J=7.5 Hz), 3.63 (3H, s), 6.6-7.3 (9H, m).

REFERENCE EXAMPLE 2

1.11 g (3.17 mmols) of 2-phenylthio-2-(3-phenoxyphenyl)propionic acid obtained in Example 6 was dissolved in 10 ml of acetic acid and the solution was heated while refluxing for 1 hour with stirring in the presence of 1.0 g of zinc powder. The solid substance present in the reaction mixture was removed by filtration and washed with methylene chloride. The combined filtrate and washing was concentrated to obtain 0.86 g of a crude product which was then purified by silica gel column chromatography eluting with diethyl etherhexane (1:5 by volume) to obtain 0.73 g (95% yield) of 2-(3-phenoxyphenyl)propionic acid. $n_D^{26}$ 1.5780.

NMR (CCl₄) δ of Product: 1.48 (3H, d, J=7 Hz), 3.62 (1H, q, J=7 Hz), 6.6-7.6 (9H, m).

REFERENCE EXAMPLE 3

1.12 g (20 mmols) of potassium hydroxide was dissolved in 10 ml of methanol in an argon atmosphere, and 0.6 g (5.45 mmols) of thiophenol was added to the solution while stirring under cooling with water. After 10 minutes, a solution of 1.16 g (5 mmols) of α-1-trichloromethyl-1-(2-thienyl)ethanol dissolved in 3 ml of methanol was added to the mixture. After 10 minutes, the temperature of the mixture was gradually increased and then heated under refluxing for 2 hours with vigorous stirring. The mixture was then cooled to room temperature, and most of the solvent was removed by distillation under reduced pressure. Diethyl ether was added to the residue and the mixture was decomposed with dilute hydrochloric acid. The ether layer was separated, washed with water, dried over anhydrous magnesium sulfate and filtered. The filtrate was concentrated under reduced pressure, and the residue was purified by silica gel column chromatography eluting with ethyl acetate-n-hexane (1:4 by volume) to obtain 940 mg (76% yield) of α-phenylthio-thiophene-2-acetic acid as a viscous oily substance.

Infrared Absorption Spectrum (cm⁻¹): 3060, 1715, 1587, 1485, 1440, 1416, 1253, 750, 705, 694.

NMR (CDCl₃) δ: 5.03 (s, 1H), 6.62-7.60 (m, 8H), 11.47 (s, 1H).

REFERENCE EXAMPLE 4

2.34 g (8.85 mmols) of α-phenylthio-α-(2-thiophene)-propionic acid was dissolved in 20 ml of acetic acid, and 1.5 g of zinc powder was added thereto followed by heat-refluxing for 30 minutes. An additional 1.5 g of zinc powder was added thereto followed by heat-refluxing for further 1.5 hours. Most of the solvent was then removed under reduced pressure, and methylene chloride was added to the residue. The solution was then filtered through Celite to remove solid substance. The filtrate was then concentrated and purified by silica gel column chromatography eluting with diethyl etherhexane (1:10 by volume) to obtain 1.28 g (92% yield) of α-(2-thiophene)propionic acid as a colorless oily substance. NMR (CCl₄) δ: 1.60 (3H, d, J=7 Hz), 3.93 (1H, q, J=7 Hz), 6.67-6.87 (2H, m), 7.07 (1H, m).

While the invention has been described in detail and with reference to specific embodiments thereof, it will be apparent to one skilled in the art that various modifications and changes can be made therein without departing from the spirit and the scope thereof.

What is claimed is:

1. A process for preparing a 2-thio-2-substituted-alkanoic acid derivative represented by the formula (I)

wherein A represents (1) a substituted-phenyl group of the formula

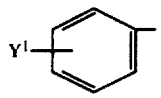

in which Y$^1$ represents an unsubstituted- or substituted-phenoxy group wherein the substituent is a halogen atom, a trifluoromethyl group or an alkoxy group having 1 to 4 carbon atoms, or (2) a substituted-thienyl group of the formula

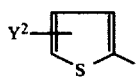

in which Y$^2$ represents an alkyl group having 1 to 4 carbon atoms; R represents an alkyl group having 1 to 4 carbon atoms; R$^3$ represents a phenyl group, an alkylphenyl group wherein the alkyl group has 1 to 4 carbon atoms, or an alkyl group having 1 to 4 carbon atoms; and R$^4$ represents a hydrogen atom or an alkyl group having 1 to 4 carbon atoms, which comprises condensing an aldehyde compound of the formula (V)

A—CHO     (V)

wherein A is as defined above, with a haloform of the formula CHX$_3$ wherein X represents a halogen atom and a mercaptan compound of the formula (IV)

R$^3$SH     (IV)

wherein R$^3$ is as defined above, in the presence of a base to produce a 2-(arylthio or alkylthio)-2-substituted-acetic acid of the formula (III)

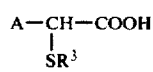

wherein A and R$^3$ are as defined above, and reacting the resulting 2-(arylthio or alkylthio)-2-substituted-acetic acid with an alkylating agent represented by the formula (II)

RZ     (II)

wherein R is as defined above, and Z represents a halogen atom, an alkyl- or arylsulfonyloxy group or a sulfuric acid ester residual group, in the presence of at least 2 mols of a base per mol of the 2-(arylthio or alkylthio)-2-substituted acetic acid, to form the compound of the formula (I) wherein R$^4$ represents a hydrogen atom and, optionally, converting the resulting compound to the compound of the formula (I) wherein R$^4$ represents an alkyl group by esterification.

2. The process according to claim 1, wherein said condensing is conducted using about 4 to about 10 mols of a base at a temperature of about 0° to about 100° C. for a period of about 1 to about 30 hours.

3. The process according to claim 1, wherein said condensing is conducted using about 1 to about 5 mols of said haloform and about 1 to about 3 mols of said mercaptan compound, per mol of said aldehyde compound of the formula (V).

4. The process according to claim 1, wherein said alkylating is carried out at a temperature of about −40° C. to room temperature for a period of about 1 to about 5 hours in the presence of a solvent.

5. The process according to claim 1, wherein said alkylating agent is used in an amount of about 1 to about 1.5 mol per mol of said 2-(arylthio or alkylthio)-2-substituted-acetic acid.

6. The process of claim 1, 2, 3, 4 or 5 wherein A represents the substituted phenyl group.

7. The process of claim 1, 2, 3, 4 or 5 wherein A represents the substituted-thienyl group.

* * * * *